United States Patent
Gaboardi et al.

(10) Patent No.: US 9,845,335 B2
(45) Date of Patent: Dec. 19, 2017

(54) SOFOSBUVIR IN CRYSTALLINE FORM AND PROCESS FOR ITS PREPARATION

(71) Applicant: HC-PHARMA AG, Zug (CH)

(72) Inventors: Mauro Gaboardi, Novara (IT); Marta Castaldi, Sizzano (IT); Graziano Castaldi, Briona (IT); Sara Helmy, Alexandria (EG)

(73) Assignee: HC-PHARMA AG, Zug (CH)

( * ) Notice: Subject to any disclaimer, the term of this patent is extended or adjusted under 35 U.S.C. 154(b) by 0 days.

(21) Appl. No.: 15/308,253

(22) PCT Filed: Jul. 29, 2015

(86) PCT No.: PCT/EP2015/067422
§ 371 (c)(1),
(2) Date: Nov. 1, 2016

(87) PCT Pub. No.: WO2016/016327
PCT Pub. Date: Feb. 4, 2016

(65) Prior Publication Data
US 2017/0051004 A1    Feb. 23, 2017

(30) Foreign Application Priority Data

Aug. 1, 2014 (IT) ................................ MI2014A1411

(51) Int. Cl.

| | | |
|---|---|---|
| *A01N 43/04* | (2006.01) | |
| *A61K 31/70* | (2006.01) | |
| *C07H 19/10* | (2006.01) | |
| *C07F 9/6558* | (2006.01) | |
| *G01L 15/00* | (2006.01) | |
| *G01L 27/00* | (2006.01) | |
| *A61K 31/7068* | (2006.01) | |
| *A61K 31/706* | (2006.01) | |
| *C07H 1/06* | (2006.01) | |
| *A61K 31/7064* | (2006.01) | |
| *A61K 31/7072* | (2006.01) | |
| *C07H 19/06* | (2006.01) | |

(52) U.S. Cl.
CPC ......... *C07H 19/10* (2013.01); *C07F 9/65586* (2013.01); *G01L 15/00* (2013.01); *G01L 27/002* (2013.01); *G01L 27/007* (2013.01); *A61K 31/706* (2013.01); *A61K 31/7064* (2013.01); *A61K 31/7068* (2013.01); *A61K 31/7072* (2013.01); *C07H 1/06* (2013.01); *C07H 19/06* (2013.01)

(58) Field of Classification Search
None
See application file for complete search history.

(56) References Cited

U.S. PATENT DOCUMENTS 8,618,076 B2    12/2013    Ross et al.

OTHER PUBLICATIONS

International Search Report for International Application No. PCT/EP2015/067422 (2 Pages) dated Oct. 1, 2015.

*Primary Examiner* — Patrick T Lewis
(74) *Attorney, Agent, or Firm* — Lucas & Mercanti, LLP

(57) ABSTRACT

Sofosbuvir in crystalline Form α, process for its production and use in pharmaceutical compositions.

9 Claims, 1 Drawing Sheet

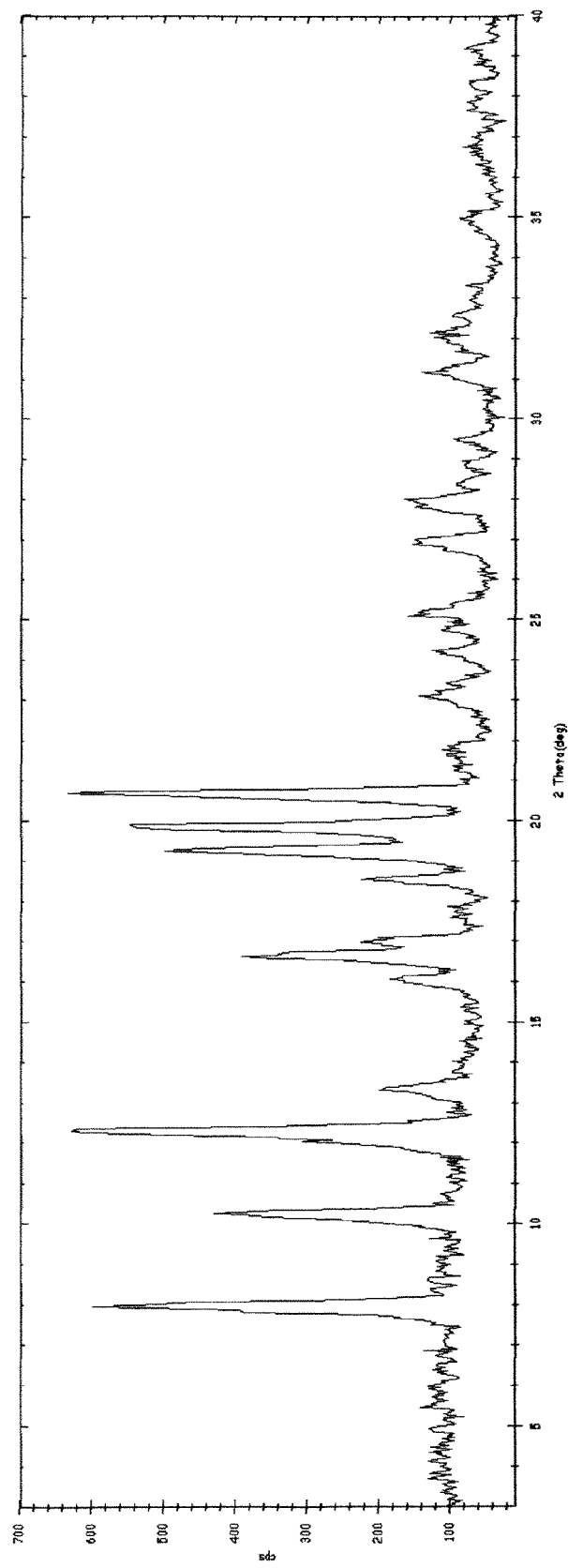

SOFOSBUVIR IN CRYSTALLINE FORM AND PROCESS FOR ITS PREPARATION

CROSS-REFERENCE TO RELATED APPLICATIONS

This application is a 371 of PCT/EP2015/067422 filed Jul. 29, 2015, which claims the benefit of Italian Patent Application No. MI02014A001411, filed Aug. 1, 2014.

FIELD OF THE INVENTION

The present invention relates to a stable polymorphic form of Sofosbuvir and a method for its preparation.

BACKGROUND OF THE INVENTION

Sofosbuvir is a prodrug used for the treatment of hepatitis C.

Hepatitis C is an infectious disease caused by Hepatitis C virus (HCV) which affects primarily the liver. The infection is often asymptomatic but its chronic infection can lead to the scarring of the liver and finally to cirrhosis, which is generally apparent after many years. In some cases the liver cirrhosis can develop liver failure, liver cancer, esophageal and gastric varices. HCV is transmitted primarily by direct contact with infected blood, often caused by intravenous drug use, poorly sterilized equipment and blood transfusions.

Hepatitis C virus causes a chronic infection in 50-80% of the peoples who are infected with, among them about 40-80% is treated. In general, the pharmacological treatment is recommended in patients with liver changes caused by virus; the reference treatment is a combination of pegylated interferon alpha and ribavirin to be taken for a period of 24 or 48 weeks, depending on the HCV virus genotype. It is observed that this treatment leads to improvements in 50-60% of cases. In phenotypes which are more difficult to be treated these two drugs are used in combination with boceprevir and telaprevir bringing the cure rate from 40% to 70%. The side effects of the treatment are frequent: half patients have flu like symptoms and one third has emotional problems, moreover the treatment carried out during the first six months is more effective than once hepatitis C has become chronic. Sofosbuvir is a drug for the treatment of hepatitis C, approved at the beginning of the year by EMA, it is taken orally and acts with a direct mechanism of action on the life cycle of the virus abolishing its replication as being a prodrug inhibitor pan-genotype of RNA polymerase NS5B RNA-dependent of HCV, it can be incorporated into HCV RNA NS5B polymerase and acts as a chain terminator.

Sofosbuvir has moreover shown a reduced number of complications of the liver disease and a reduced number of adverse effects than patients undergoing other treatments.

Sofosbuvir is a compound of formula (I)

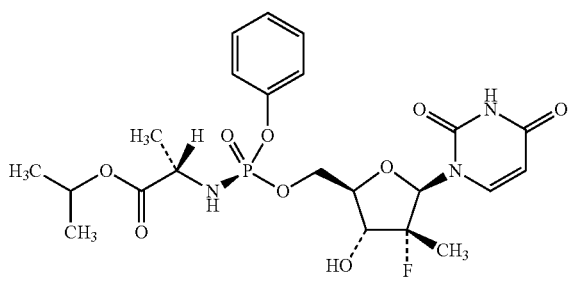 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

chemically known as isopropyl (2S)-2-[[[(2R,3R,4R,5R)-5-(2,4-dioxopyrimidine-1-yl)-4-fluoro-3-hydroxy-4-methyl-tetrahydrofuran-2-yl]methoxy-phenoxy-phosphoryl]-aminopropanoate, marketed as Sovaldi® and described in U.S. Pat. No. 8,563,530.

Some polymorphic forms of Sofosbuvir are known in the literature.

U.S. Pat. No. 8,618,076 describes crystalline, hydrated and solvated forms of Sofosbuvir, named as Form 1 (crystalline), Form 2 (crystalline), Form 3 (chloroform solvate), Form 4 (hydrate), Form 5 (crystalline) and Form 6 (crystalline) and describes also two amorphous forms.

Polyphormism is the property of the molecules to assume more than one crystalline or amorphous form in their solid state. Some substances are know to exist in only one crystalline or amorphous form; others indeed can have two or more crystalline forms. Polymorphs are different solids with the same molecular formula but with different physical properties that can be advantageous or disadvantageous compared with the other polymorphic forms of the same family.

The morphology of organo-chemical active ingredients is important for their pharmaco chemical development. A crystalline form, compared to other crystalline forms, can have many advantages. A suitable process for a crystalline form can give to active ingredient's manufacturers several advantages, such as, the use of steps or solvents cheap or with a low environmental impact, higher yields and higher purity of the desired product.

The polymorphism, the number of crystalline forms of an organo-chemical compound, their stability and their behavior in a living organism are never predictable. The different polymorphs of a compound have different energies of the crystal lattice and show in this way, different physical properties of the solid state (such as shape, density, melting point, colour, stability, dissolution rate, ease of grinding, granulation etc.). In polymorphism, these morphological differences can have drastic effects on the flowability of the ground solid (the flowability regards the easiness whereby the material is treated during the processing into a pharmaceutical product), on shipping and storage stability of different forms of administration, on the ability to produce different forms of administration, on solubility in polar or non polar, protic or aprotic solvents, on solubility in aqueous solutions, on solubility in gastric juices, on blood solubility and finally on bioavailability.

The dissolution rate of an active ingredient in the gastric fluid of a patient can have therapeutical effects because it determines the maximum concentration that an active ingredient can reach in the blood by oral administration. Other important properties of polymorphic forms affect the easiness of transforming the active ingredient form in pharmaceutical dosages, on the flowability of a powder or a granulate form and the surface properties that determine if the crystals of the form will stick each other once compressed in a tablet.

A polymorphic form can have a different thermic behavior compared to an amorphous form or any other polymorphic form. Thermic behavior can be measured in laboratory through techniques such as capillary melting point and differential scanning calorimetry (DSC) and can be used to distinguish various polymorphic forms. A polymorphic form can have different spectroscopical properties that can be detected trough the X-Ray Powder diffraction (XRPD).

The discovery of new polymorphic forms of a pharmaceutical compound gives another possibility to improve the characteristics of said product. An expert of pharmaceutical techniques extends his/her knowledge of forms useful for the development of a pharmaceutical form with a targeted release profile or with other characteristics such as fluidity and dissolution rate in aqueous liquids.

SUMMARY OF THE INVENTION

The aim of the present invention is to give a new stable and not hygroscopic crystalline form which can be prepared with an ease, repeatable method with excellent yields and easy industrial applicability.

We have now found a stable and not hygroscopic crystalline form of Sofosbuvir suitable for the preparation of stable pharmaceutical formulations as obtainable with a distribution of the particle sizes such to allow a good compressibility and flowability.

It is therefore object of the present invention a crystalline form of Sofosbuvir, from now on named also as Form α, characterized by an XRPD comprising peaks at about 7.96; 10.28; 12.32; 16.64; 17.00; 18.56; 19.28; 19.88; 20.72; 21.88; 23.08; 24.24; 25.16; 27.00; 27.96±0.2° 2θ according to FIG. 1.

BRIEF DESCRIPTION OF THE FIGURES

FIG. 1: XRPD of Sofosbuvir Form α.

The new polymorphic form is also characterized by a distribution of the particles sizes (PSD) where the size of the 90% of the particles is from 10 to 50 μm and by the following parameters:

| Bulk Density | 0.22 g/ml |
|---|---|
| Tapped Density | 0.29 g/ml |
| Compressibility index | 24.4 |
| Hausner ratio | 1.32 |

It is a further object of the present invention a process for the preparation of Sofosbuvir in crystalline Form α which comprises a step of dissolution of Sofosbuvir in ketones and a crystallization step of the solution obtained by said dissolution.

The ketones used for the process object of the present invention are selected among the group consisting of acetone, metyl ethyl ketone, isobutyl methyl ketone and diethyl ketone: the ketones are preferably selected among the group consisting of metyl ethyl ketone and isobutyl methyl ketone.

Preferably, said crystallization step is obtained by cooling of the solution or by a slow solvent evaporation.

DETAILED DESCRIPTION OF THE INVENTION

According to a preferred embodiment, the process of the present invention comprises the following steps:
i. dissolution of Sofosbuvir in isobutyl methyl ketone at a temperature within the range of 50-60° C.;
ii. cooling of the solution obtained from step i. to a temperature of 20° C. under stirring till the precipitation of the product;
iii. separation by filtration of the product obtained from step ii;
iv. under vacuum drying of the product obtained from step iii.

The process for the preparation of Sofosbuvir Form α according to the present invention is particularly simple and of easy industrial applicability.

Therefore, further objects of the present invention are the use of Sofosbuvir Form α as a medicament and pharmaceutical compositions containing it as an active ingredient in mixture with a suitable carrier.

All the terms used in the present application, unless otherwise indicated, are to be understood in their common meaning as known in the art. The term "about" comprises the usual experimental error of any measurement.

Although the present invention has been described in its characterizing features, their equivalents and modifications obvious to the skilled in the art are included in the present invention.

The present invention will be now illustrated through some examples without limiting it.

EXAMPLES

Diffraction spectra XRPD were carried out through a diffractometer APD 2000 Ital Structures at ambience temperature using a tube CuKa (40 Kv, 30 Ma) as X ray source. The data were collected through a 2q continuous scan at a scan speed of 0.02°/s in the range of 3°-40° in 2q.

Example 1

5 g of Sofosbuvir were suspended in 15 ml of isobutyl methyl ketone into a reaction flask under stirring, the temperature was kept at about 50/60° C. and the mixture was kept under such conditions until complete dissolution. The temperature was brought to about 20° C. and the mixture was kept under stirring for about one hour. The resultant solid was filtered and washed with isobutyl methyl ketone (2×5 ml) at the temperature of 20° C. and dried in oven under vacuum at 45-50° C. to give 4.5 g of Sofosbuvir Form α.
PSD=d(0.1):1.831 μm;
d(0.5):5.263 μm;
d(0.9):20.369 μm.

Example 2

5 g of Sofosbuvir were suspended in 15 ml of methyl ethyl ketone into a reaction flask under stirring, the temperature was brought to about 50-60° C., the reaction mixture was kept under such conditions until complete dissolution and the resultant solution was transferred into a crystallizer. The solvent was evaporated at room temperature to give 5 g of Sofosbuvir Form α.

Example 3

5 g of Sofosbuvir were suspended in 15 ml of acetone into a reaction flask under stirring, the temperature was brought to about 50-60° C., the reaction mixture was kept under such conditions until complete dissolution and the resultant solution was transferred into a crystallizer. The solvent was evaporated at room temperature to give 5 g of Sofosbuvir Form α.

The invention claimed is:
1. Sofosbuvir in crystalline Form α characterized by an XRPD comprising the following peaks: 7.96; 10.28; 12.32; 16.64; 18.56; 19.28; 19.88; 20.72; 21.88; 23.08; 24.24; 25.16; 27.00; 27.96±0.2° 2θ.

2. A process for the preparation of Sofosbuvir according to claim 1 wherein it comprises a step of dissolution of Sofosbuvir in ketones and a crystallization step of the solution obtained by said dissolution.

3. The process according to claim 2, wherein said ketones are selected from the group consisting of acetone, methyl ethyl ketone, isobutyl methyl ketone and diethyl ketone.

4. The process according to claim 2, wherein said ketones are selected from the group consisting of methyl ethyl ketone and isobutyl methyl ketone.

5. The process according to claim 2, wherein said crystallization is obtained by cooling or by solvent evaporation.

6. The process according to claim 2, wherein it comprises:
   i. dissolution of Sofosbuvir in isobutyl methyl ketone at a temperature within the range of 50-60° C.;
   ii. cooling the solution obtained from step i to a temperature of 20° C. till the precipitation of the product;
   iii. filtration of the product obtained from step ii.; and
   iv. under vacuum drying of the product obtained from step iii.

7. A pharmaceutical composition comprising Sofosbuvir according to claim 1.

8. The process according to claim 2, wherein said Sofosbuvir obtained with said process has a PSD wherein the size of the 90% of the particles is in the range of 10-50 μm.

9. The process according to claim 2, wherein said Sofosbuvir obtained with said process has the following PSD: d(0.1): 1.831 μm; d(0.5): 5.263 μm; d(0.9): 20.369 μm.

* * * * *